United States Patent
Turin et al.

(10) Patent No.: US 12,310,824 B1
(45) Date of Patent: May 27, 2025

(54) SURGICAL DRESSING FOR DRAINS

(71) Applicants: Sergey Y Turin, Scottsdale, AZ (US); Farhad Fatakia, North Arlington, VA (US)

(72) Inventors: Sergey Y Turin, Scottsdale, AZ (US); Farhad Fatakia, North Arlington, VA (US)

(73) Assignee: Sergey Y. Turin, Scottsdale, AZ (US)

( * ) Notice: Subject to any disclaimer, the term of this patent is extended or adjusted under 35 U.S.C. 154(b) by 0 days.

(21) Appl. No.: 18/670,671

(22) Filed: May 21, 2024

(51) Int. Cl.
*A61F 13/00* (2024.01)
*A61F 13/01* (2024.01)
*A61F 13/539* (2006.01)

(52) U.S. Cl.
CPC ...... *A61F 13/01029* (2024.01); *A61F 13/539* (2013.01); *A61F 2013/00412* (2013.01)

(58) Field of Classification Search
None
See application file for complete search history.

(56) References Cited

U.S. PATENT DOCUMENTS

| | | | | |
|---|---|---|---|---|
| 4,669,458 A | * | 6/1987 | Abraham | A61M 25/02 128/846 |
| 5,099,832 A | * | 3/1992 | Ward | A61F 15/001 602/41 |
| 2004/0126413 A1 | * | 7/2004 | Sigurjonsson | A61L 15/425 424/445 |
| 2011/0245778 A1 | * | 10/2011 | Chawki | A61M 25/02 604/180 |

* cited by examiner

*Primary Examiner* — Kim M Lewis
(74) *Attorney, Agent, or Firm* — Inspired Idea Solutions Law Firm (57) ABSTRACT

A surgical dressing is disclosed. The surgical dressing may have a dressing element, a connection element, and a tube element. The dressing element may be applied to a wound site of an organic body. The dressing element and tube element may be coupled at opposing ends of the connection element. The tube element may be coupled to a tube extending from the wound site. A secondary layer may be coupled to the connection element to retain the connection element in a stretched condition. The secondary layer may be removed from the connection element to enable the connection element to stretch or retract in response to forces applied to or removed from the tube.

19 Claims, 9 Drawing Sheets

SURGICAL DRESSING FOR DRAINS

FIELD

The present disclosure generally relates to surgical dressings, and more particularly to surgical dressings used in connection with tubes.

BACKGROUND

Surgical dressings have been applied medically for thousands of years. In fact, the Egyptians may have been the first civilization to use adhesive bandages (through the use of honey). In the 18$^{th}$ century, surgery finally began to be considered a separate division of medicine. Since that time, there have been vast improvements in antiseptic techniques in an effort to reduce pain and mortality.

In particular, some wound care requires the use of tubes (e.g., drain tubes) as a means of reducing foreign or infected material in a wound. The use of tubes in combination with surgical dressings is replete with problems, such as the accidental removal of the tube, unwanted forces applied to the surgical dressing (and therefore applied to the wound), pain at or around the wound site, and so forth.

Therefore, a need exists to improve performance of surgical dressings used in connection with tubes in order to reduce or eliminate these problems.

SUMMARY

A surgical dressing configured to be applied over a wound of an organic body, the surgical dressing located in proximity to a tube, the surgical dressing comprising: a dressing element adhered to the organic body, a connection element extending from the dressing element along the tube, wherein the connection element is elastic, and a tube element extending from the connection element, the tube element coupled to the tube, wherein the connection element is capable of stretching to absorb a force exerted on the tube.

A surgical dressing configured to be applied over a wound of an organic body, the surgical dressing located in proximity to a tube, the surgical dressing comprising a dressing element adhered to the organic body, a connection element extending from the dressing element along the tube, wherein the connection element is elastic, a tube element extending from the connection element, the tube element coupled to the tube, and a secondary layer adhered along the length of the connection element, wherein the connection element is capable of stretching to absorb a force exerted on the tube after the secondary layer is removed.

A method of manufacturing a tube connection apparatus configured to be applied to a surgical dressing applied over a wound of an organic body in proximity to a tube, the method comprising forming a connection element capable of extending along the tube, wherein the connection element is elastic, and forming a tube element extending from the connection element, the tube element capable of being coupled to the tube, wherein the connection element is capable of stretching to absorb a force exerted on the tube.

BRIEF DESCRIPTION OF THE DRAWINGS

Various aspects and advantages will become apparent upon review of the following detailed description and upon reference to the drawings in which.

DETAILED DESCRIPTION

The following disclosure includes a method and apparatus for a surgical dressing applied to a wound in the proximity of a tube. The surgical dressing may be applied at a wound site (e.g., on an appendage of an organic body). The surgical dressing may have a dressing element, a connection element, and a tube element. The tube may extend out of the organic body from a wound site. The tube may be a drain tube, a catheter tube, an IV tube, a central line, a monitoring line, and so forth (any wire or tube-like object exiting the organic body).

The dressing element may be applied at the wound site. The wound site may be the result of accidental or intentional damage to the organic body. A wound site may be the result of injury. A wound site may be the result of creating a surgical incision to enable the entry of a tube (e.g., a tube entry site). The dressing element may have a slot formed in the dressing element that extends from a perimeter portion of the dressing element into an interior portion of the dressing element.

The connection element may be coupled to the dressing element at a first end and to the tube element at a second end. The connection element may have a length dimension greater than, equal to, or less than the length of the slot. The second end of the connection element may be positioned beyond the slot outside the perimeter of the dressing element. While the connection element may have a relatively long length and narrow width, the tube element may have a relatively short length and wide width. Opposing ends of the tube element may be configured to wrap around the tube.

During installation a tube may be inserted into a wound. The dressing element may be applied onto the wound site around the tube. The connection element may be oriented along the tube. The tube element may be coupled to the tube. In this way, the tube may be secured against removal or being pulled out of the wound. If force is applied to tube, that force will be resisted by surgical dressing.

Figure 1:
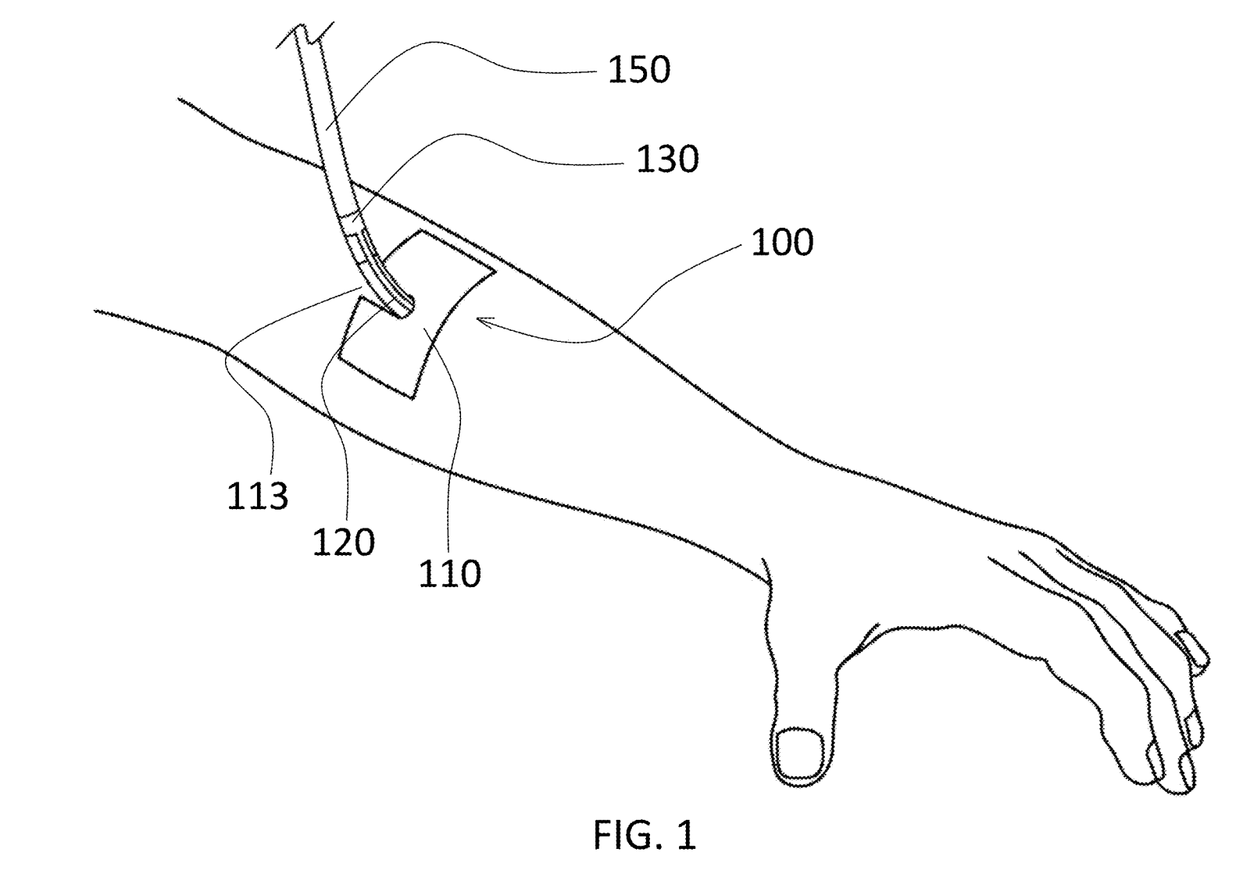
FIG. 1 illustrates an isometric view of a surgical dressing applied to a wound around a tube.

FIG. 1 illustrates an isometric view of a surgical dressing 100 applied to a wound (e.g., wound 399 of FIG. 3) around a tube 150. The surgical dressing 100 may have a dressing element 110, a connection element 120, and a tube element 130.

The surgical dressing 100 is exemplified as applied at a wound site on an arm of an injured person, however, the present disclosure contemplates the use of the surgical dressing 100 at any wound site throughout an organic body (e.g., a human body). This disclosure contemplates the use of the surgical dressing in connection with any number of drain types, such as one or more of a Jackson-Pratt (JP)

drain, a Blake drain, a Penrose drain, a negative pressure drain, a Redivac drain, a Shirley drain, a pigtail drain, and so forth.

The tube 150 may extend from within the organic body, through the wound site, and outward to an exterior of the organic body. Once outside the organic body, the tube 150 may terminate at a bag or bottle used to collect exiting fluids and materials (e.g., a closed drain system).

Dressing element 110 may be applied at a wound site. Dressing element 110 may be substantially planar (e.g., flat) before being applied at a wound site (e.g., when in its product packaging. Dressing element 110 may be formed of material capable of bending, flexing, and/or conforming (e.g., to conform to the shape of the organic body and/or to the wound when applied at the wound site). Dressing element 110 may have a particular shape (e.g., square as exemplified in FIG. 1). Dressing element 110 may include multiple layers having different characteristics, such as one or more of an outer layer, a middle layer, a contact layer, a structural layer, an antibacterial layer, an absorbent layer, a padded layer, a compression bandage layer, a semipermeable layer, a shape-conforming layer, and so forth. A single layer may contain one or more of the above characteristics (e.g., an outer layer may be semipermeable, a middle layer may be padded and absorbent, a contact layer may be antibacterial, and so forth). Dressing element 110 may be formed of various materials suited for wound care, such as one or more of gauze, lint, cotton, wool, plasters, synthetic polymers, and so forth.

Dressing element 110 may have a slot 113 formed in the dressing element 110. Slot 113 may extend from a perimeter portion of dressing element 110 into an interior portion of dressing element 110 (e.g., to an approximate middle of dressing element 110). Slot 113 may extend through all the layers of dressing element 110. Slot 113 may extend about half way through dressing element 110. Slot 113 may extend a length into dressing element 110. Slot 113 may have a width corresponding to a diameter of tube 150. Slot 113 may have a width larger than a diameter of tube 150 (e.g., between 100% and 200% of the diameter of tube 150).

Connection element 120 may be coupled to dressing element 110. Connection element 120 may be connected to dressing element 110 near a middle of dressing element 110. Connection element 120 may be connected to dressing element 110 at a position within slot 113. Connection element 120 may be connected at an end of slot 113 away from the perimeter portion of dressing element 110.

Connection element 120 may have a length dimension extending from an end adjacent dressing element 110 to an opposing end. The length dimension may be about the length of slot 113. The length dimension may be greater than or equal to the length of slot 113. The length dimension may be substantially greater than the length of slot 113 (e.g., twice the length of slot 113, or more). The opposing end of connection element 120 may be positioned at the perimeter portion of dressing element 110. The opposing end of connection element 120 may be positioned beyond slot 113. The opposing end of connection element 120 may be positioned beyond the perimeter portion of dressing element 110. Connection element 120 may have a width dimension. The width dimension may be about the width of slot 113. The width dimension may be less than or equal to the width of slot 113. The width dimension may be substantially less than the width of slot 113 (e.g., half the width of slot 113, or less).

Tube element 130 may be coupled to connection element 120. Connection element 120 may be coupled to dressing element 110 at a first end and coupled to tube element 130 at a second end. The second end may be opposite of the first end. Connection element 120 may be coupled to tube element 130 at or near a midpoint of tube element 130 (e.g., as exemplified in FIG. 2). Connection element 120 may be coupled to tube element 130 at an endpoint of tube element 130.

Tube element 130 may have a length dimension extending from an end adjacent connection element 120 to an opposing end. Tube element 130 may have a width dimension extending orthogonally of the length dimension. The width dimension may be greater than the length dimension. The width dimension may be between one and twenty times the length dimension (e.g., about 10 times). The length dimension of tube element 130 may be less than the length of connection element 120. The length dimension may be between one and twenty times less than the length of connection element 120 (e.g., about 10 times). The opposing ends of tube element 130 may be positioned oppositely of the connection with connection element 120.

The opposing ends of tube element 130 may be configured to wrap around tube 150. Tube element 130 may be coupled around tube 150. Tube element 130 may be secured to tube 150. Tube element 130 may be adhered to tube 150 (e.g., such as with the use of adhesive, peel-and-stick tape, clasp, clip, or other fastening means).

During installation a tube 150 may be inserted into a wound. Dressing element 110 may be applied onto the wound site around the tube 150. Dressing element 110 may seal or substantially seal around tube 150. Connection element 120 may be oriented along the tube 150 (e.g., extending parallel to tube 150, extending along a surface of tube 150, and/or placed in an abutting relationship with tube 150). Tube element 130 may be coupled to tube 150 (e.g., securing at a discrete position along the length of tube 150 and configured to be retained to tube 150 without slipping away from this discrete position). In this way, tube 150 may be secured against removal or being pulled out of the wound by surgical dressing 100. If force is applied to tube 150, that force will be resisted by connection element 120.

Figure 2:
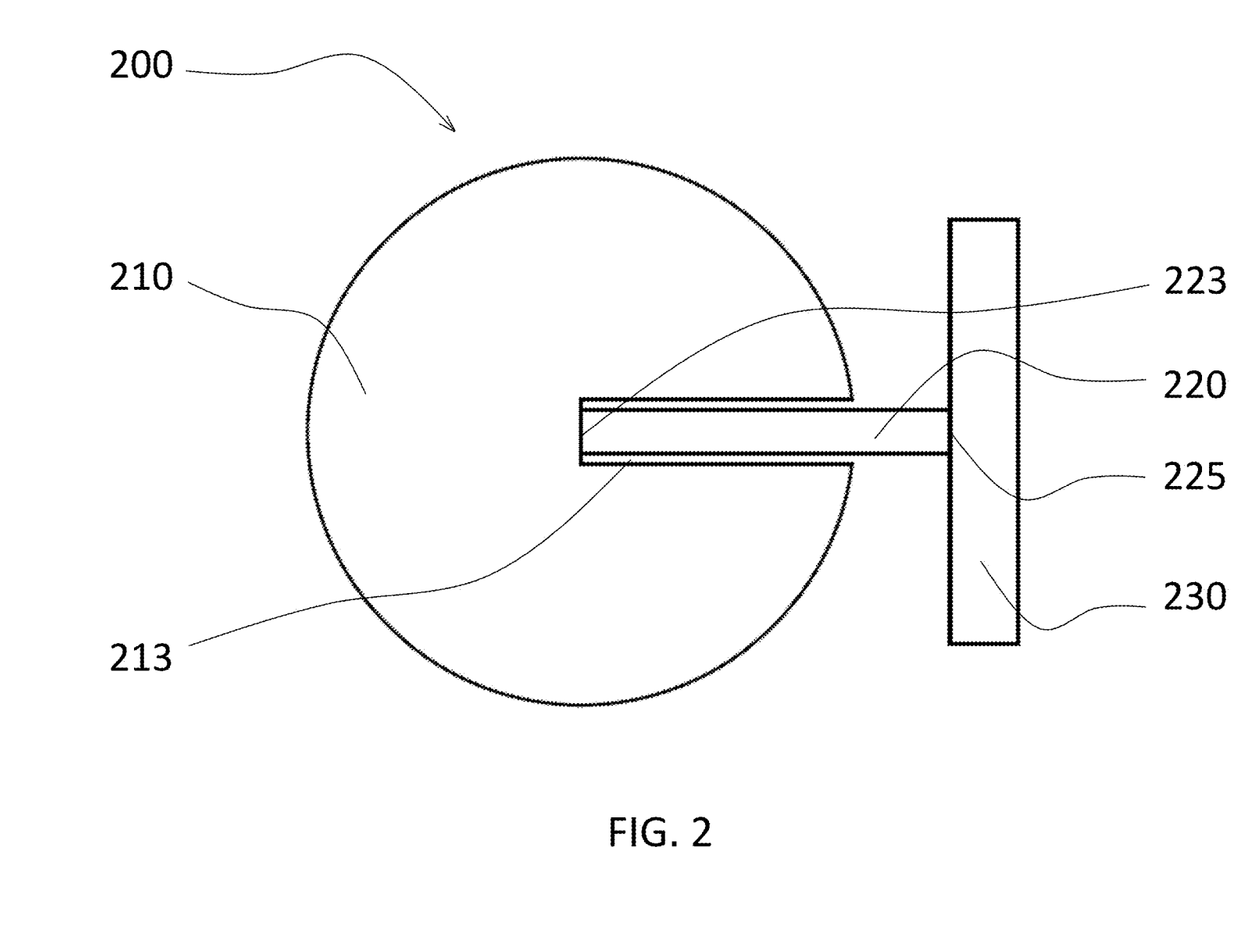
FIG. 2 illustrates a top view of a surgical dressing.

FIG. 2 illustrates a top view of a surgical dressing 200 having a dressing element 210, a connection element 220, and a tube element 230. A slot 213 may be formed in dressing element 210. Slot 213 may extend from an outer perimeter of dressing element 210 to a discrete location within the interior of dressing element 210 (e.g., a position corresponding to the middle of dressing element 210). Dressing element 210 may have a particular shape (e.g., circular as exemplified in FIG. 1), though any shape is possible that facilitates attachment of dressing element 210 to different kinds of wounds (e.g., square, rectangle, triangle, circle, oval, butterfly-shaped, and so forth).

Dressing element 210 and tube element 230 may be coupled on opposing ends of connection element 220 (e.g., at one or more connection points). Connection element 220 may be secured to dressing element 210 at connection point 223. Connection element 220 may be secured to tube element 230 at connection point 225. While connection points 223, 225 are exemplified as lines of intersection, the connection point may be at a point, along a line (e.g., linear or nonlinear), or across an area (e.g., as exemplified in FIG. 4). The connection may be facilitated by adhesive, thread (e.g., a seam), weld, or by any other means for connecting two different elements.

Connection element 220 may be formed of similar or different material to dressing element 210. Connection element 220 may be formed of similar or different material to tube element 230. Connection element 220 may be formed of a material with a high level of elasticity (e.g., between 10% and 100% stretch, or more, where stretch may be measured as a percent change in dimension in response to the application of force when compared to the dimension with no force applied). Connection element 220 may be formed of one or more of polypropylene, polyester, nylon, satin, polyester, velvet, lycra, lace, cotton, spandex, denim, wool, elastane, chiffon, neoprene, rubber, and vinyl. Connection element 220 may be formed of synthetic material. The elasticity of connection element 220 may enable connection element 220 to stretch and/or retract in response to forces exerted on a tube (e.g., tube 150 of FIG. 1).

While connection element 220 is exemplified as being attached along edges of dressing element 210 and/or tube element 230, this disclosure contemplates attachment at other positions away from the edges of dressing element 210 and/or tube element 230.

Figure 3:
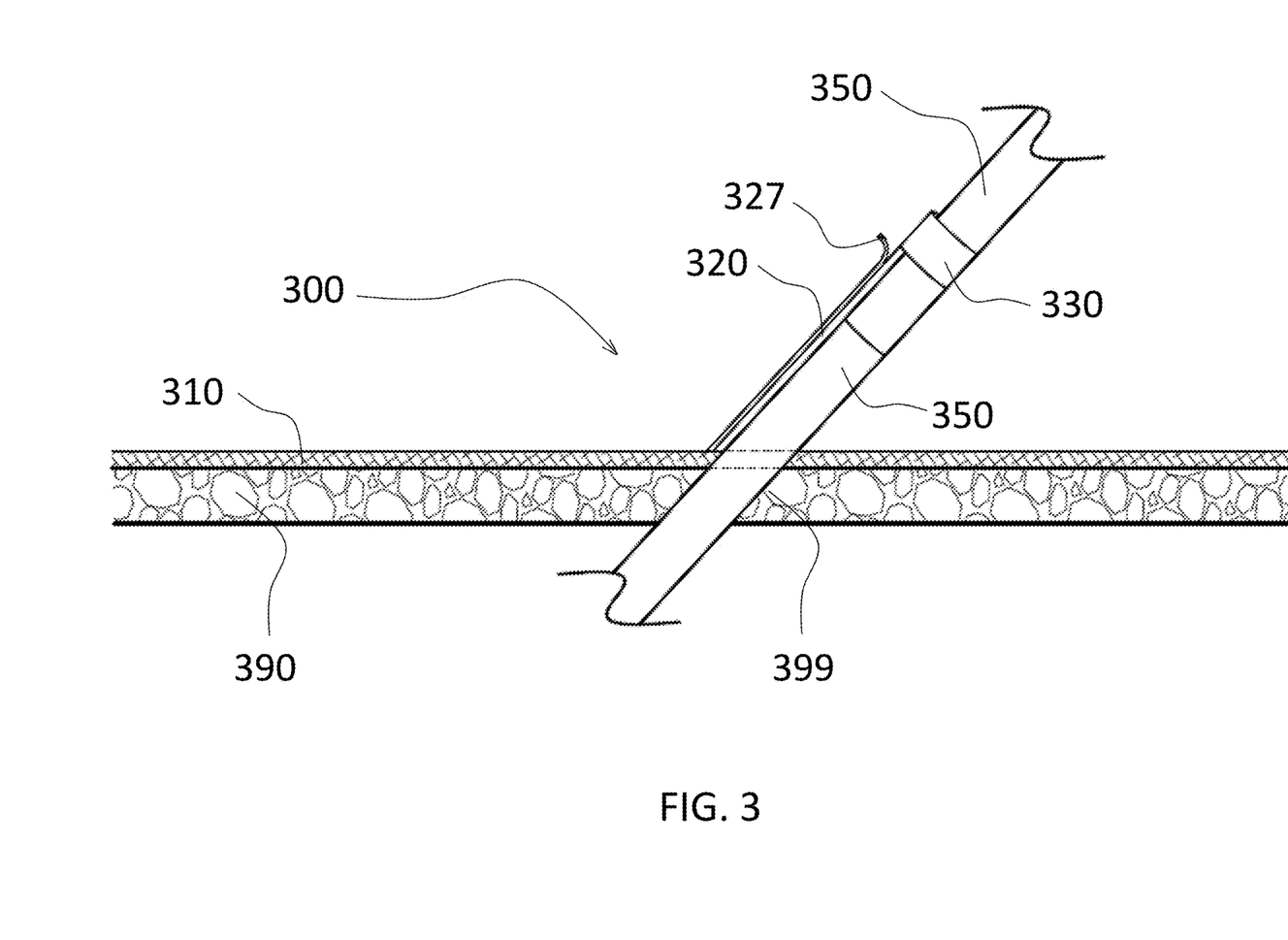
FIG. 3 illustrates a cross-sectional view of a wound with a surgical dressing applied over the wound and a tube extending out of the wound.

FIG. 3 illustrates a cross-sectional view of a wound 399 with a surgical dressing 300 applied over the wound 399 and a tube 350 extending out of the wound 399. Tube 350 may extend into an organic body (e.g., through a skin layer 390). Surgical dressing 300 may be applied to an exterior of skin layer 390 around tube 350 as represented in this disclosure.

Surgical dressing 300 may have a dressing element 310, a connection element 320, and a tube element 330. Dressing element 310 may be applied to an exterior of skin layer 390 around tube 350. Connection element 320 may extend from dressing element 310 to tube element 330. Tube element 330 may be coupled around tube 350 at a discrete location on tube 350.

Connection element 320 may be formed of an elastic material and may stretch or retract in response to forces exerted on tube 350. A secondary element 327 may extend along connection element 320. Secondary element 327 may be adhered to connection element 320 (e.g., along all or substantially all of the length of connection element 320). Secondary element 327 may be affixed to connection element 320 (e.g., pinned at opposing ends). Secondary element 327 may be non-elastic and/or may have a low elasticity (e.g., between 0% and 10% stretch). Secondary element 327 may be capable of deformation (e.g., bending). Secondary element 327 may be removed from connection element 320 before or after surgical dressing 300 is applied over wound 399.

Secondary element 327 may enable connection element 320 to be pre-loaded with tensile forces (e.g., prior to application of surgical dressing 300 to the organic body). Secondary element 327 may be applied to connection element 320 while connection element 320 is in a stretched condition. Secondary element 327 may hold connection element 320 in the stretched condition until secondary element 327 is removed from connection element 320 (e.g., during application of surgical dressing 300 to the organic body). The stretched condition may correspond to a maximum stretch of connection element 320 without causing permanent damage to connection element 320. The stretched condition may correspond to an intermediate stretch of connection element 320 (e.g., between no stretch and the maximum stretch without causing damage to connection element 320). The stretched condition may correspond to a desired length of connection element 320 (e.g., such as a length corresponding to between a 10% and a 100% stretch, or more). The stretched condition may correspond to a desired amount of tensile and/or pre-loaded force (e.g., such as a force of between 10 lbs. and 0.1 lbs. or less).

During installation a tube 350 may be inserted into a wound. Dressing element 310 may be applied onto the wound site around the tube 350. Connection element 320 may be oriented along the tube 350. Tube element 330 may be coupled to tube 350. Secondary element 327 may be removed (e.g., pulled, peeled, snapped, snipped, or lifted) from connection element 320. Removal of secondary element 327 may cause or allow connection element 320 to apply a force to tube 350 (e.g., where connection element 320 is pre-loaded with tensile forces, removal of secondary element 327 may release connection element 320 and allow a tensile force to be exerted on tube 350). In this way, tube 350 may be retained within wound 399 and prevented from being pulled out of wound 399. If an opposing force is applied to tube 350, that force will be resisted by connection element 320 due to the pre-loaded tensile force of connection element 320.

Practically speaking, tube 350 may experience some movement in the event that forces are applied to it during use. The elastic nature of connection element 320 may allow a limited range of movement of tube 350 (e.g., absorbing some or all of the forces exerted on the tube 350 while limiting forces exerted on the dressing element 310 and/or the organic body), but may prevent too much movement of tube 350 while alleviating any discomfort experienced by the organic body.

Figure 4:
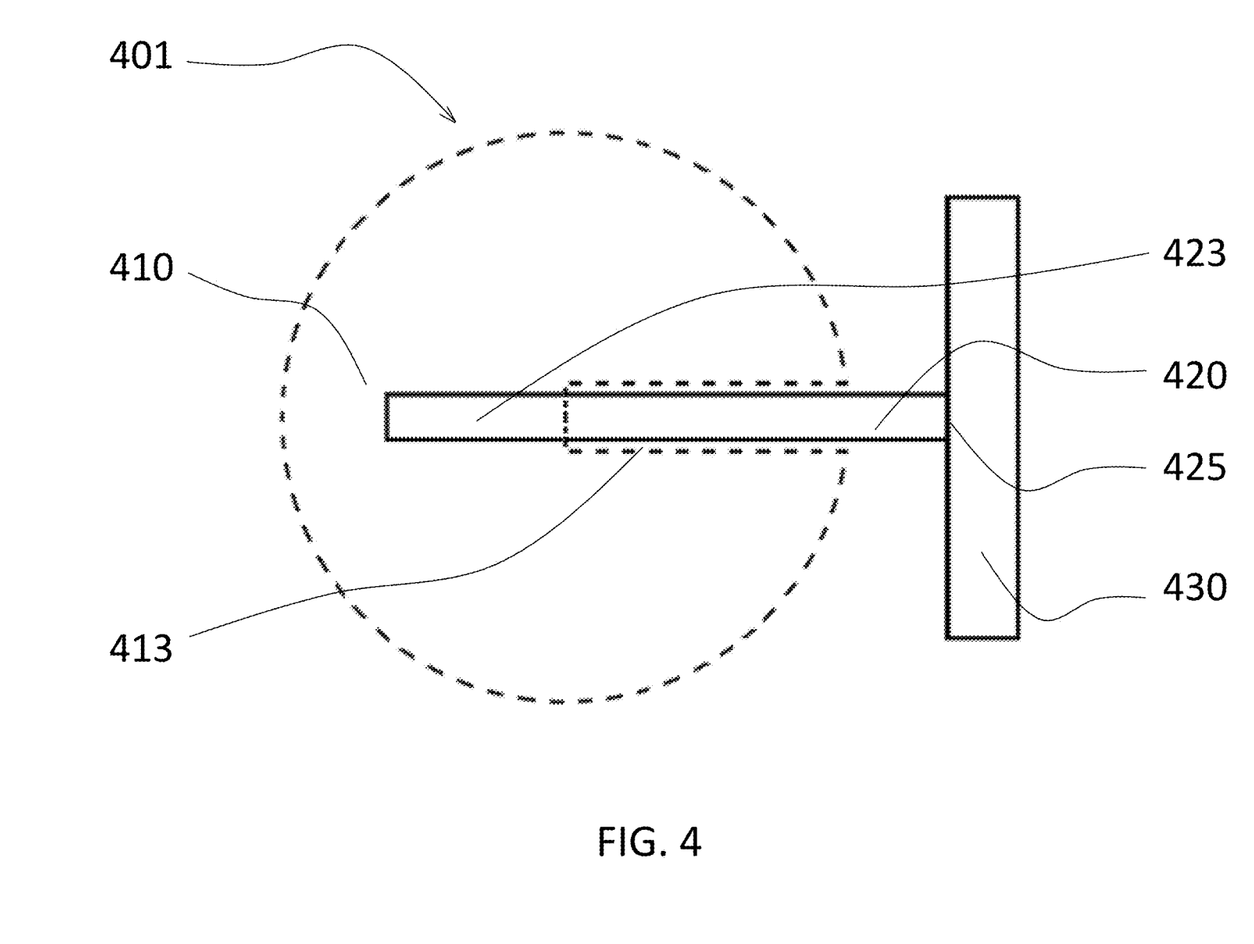
FIG. 4 illustrates a tube connection apparatus capable of attachment to a surgical dressing.

FIG. 4 illustrates a top view of a tube connection apparatus 401 capable of attachment within a slot 413 of a surgical dressing 410, shown in broken lines (e.g., similar to dressing element 210 of FIG. 2). The tube connection apparatus 401 may include a connection element 420 and a tube element 430. A first end of connection element 420 may be coupled to tube element 430 at a connection point 425. The first end of connection element 420 may be coupled at a midpoint of tube element 430, though other positions along tube element 430 are contemplated by this disclosure. Connection element 420 may extend to a second end. The second end may be positioned oppositely of tube element 430.

During use of the tube connection apparatus 401, the second end of connection element 420 may be coupled to a surgical dressing 410 (e.g., at connection point 423, represented by an elongated portion of connection element 420 having a surface area that is adhered to surgical dressing 410). The second end of connection element 420 may be coupled to a surgical dressing 410 before or after application of surgical dressing 410 to a wound. The in-situ application of tube connection apparatus 401 to surgical dressing 410 may be accomplished by various connection means, such as adhesive, thread (e.g., a seam), weld, clamping, or by any other means for connecting two different elements.

Figure 5:
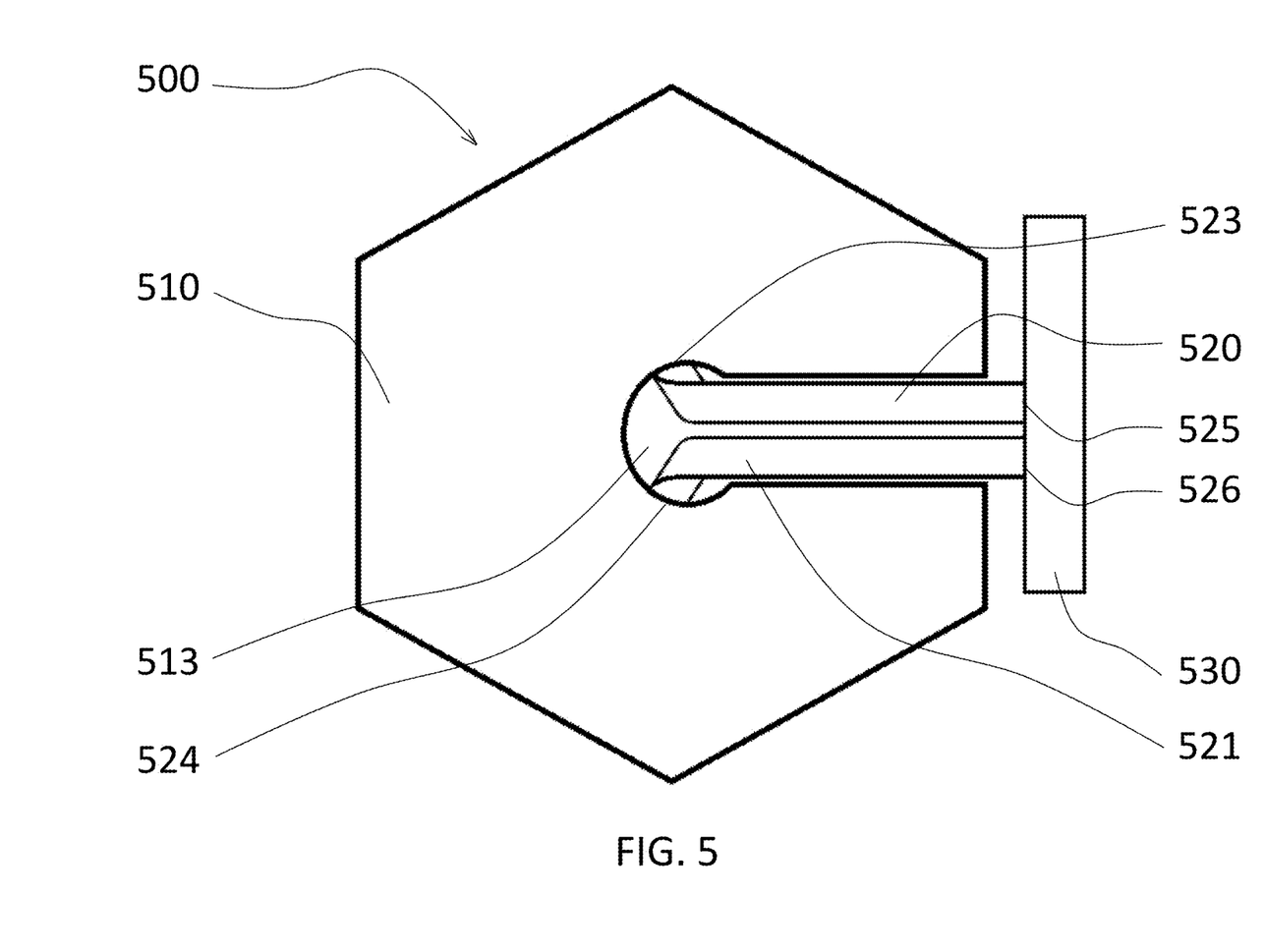
FIG. 5 illustrates a top view of a surgical dressing.

FIG. 5 illustrates a top view of a surgical dressing 500 having a dressing element 510, a plurality of connection elements, and a tube element 530. The plurality of connection elements may include 1, 2, 3, 4, 5, 6, 7, 8, or more connection elements. The plurality of connection elements may include a first connection element 520 and a second connection element 521.

A slot 513 may be formed in dressing element 510. Slot 513 may extend from an outer perimeter of dressing element 510 to a discrete location within the interior of dressing element 510 (e.g., approximately a center of dressing element 510). Dressing element 510 may have a particular shape (e.g., hexagonal), though any shape is possible that facilitates attachment of dressing element 510 to different kinds of wounds. Slot 513 may be wide enough to accommodate a tube exiting a wound of an organic body. Slot 513 may have a constant width, as exemplified in FIG. 2. Slot 513 may have an irregular width. Slot 513 may have a wider end and a narrower end, as exemplified in FIG. 5.

The plurality of connection elements may extend from within slot 513 to tube element 530. The plurality of connection elements may be secured at a common position within slot 513 (e.g., at a single connection point). The plurality of connection elements may be secured around a perimeter of slot 513 (e.g., at a plurality of connection points). The plurality of connection elements may be regularly or irregularly spaced within slot 513. The first connection element 520 may be positioned oppositely of the second connection element 521 within slot 513. The first connection element 520 may be secured to the dressing element 510 at a first connection point 523 as described in this disclosure. The second connection element 521 may be secured to the dressing element 510 at a second connection point 524 as described in this disclosure.

The plurality of connection elements may extend to a common tube element 530. The plurality of connection elements may be of approximately the same length, and may retain tube element 530 (e.g., and a tube) at a predetermined distance or position with respect to dressing element 510. The first connection element 520 may be secured to tube element 530 at a third connection point 525 as described in this disclosure. The second connection element 521 may be secured to tube element 530 at a fourth connection point 526 as described in this disclosure.

Figure 6:
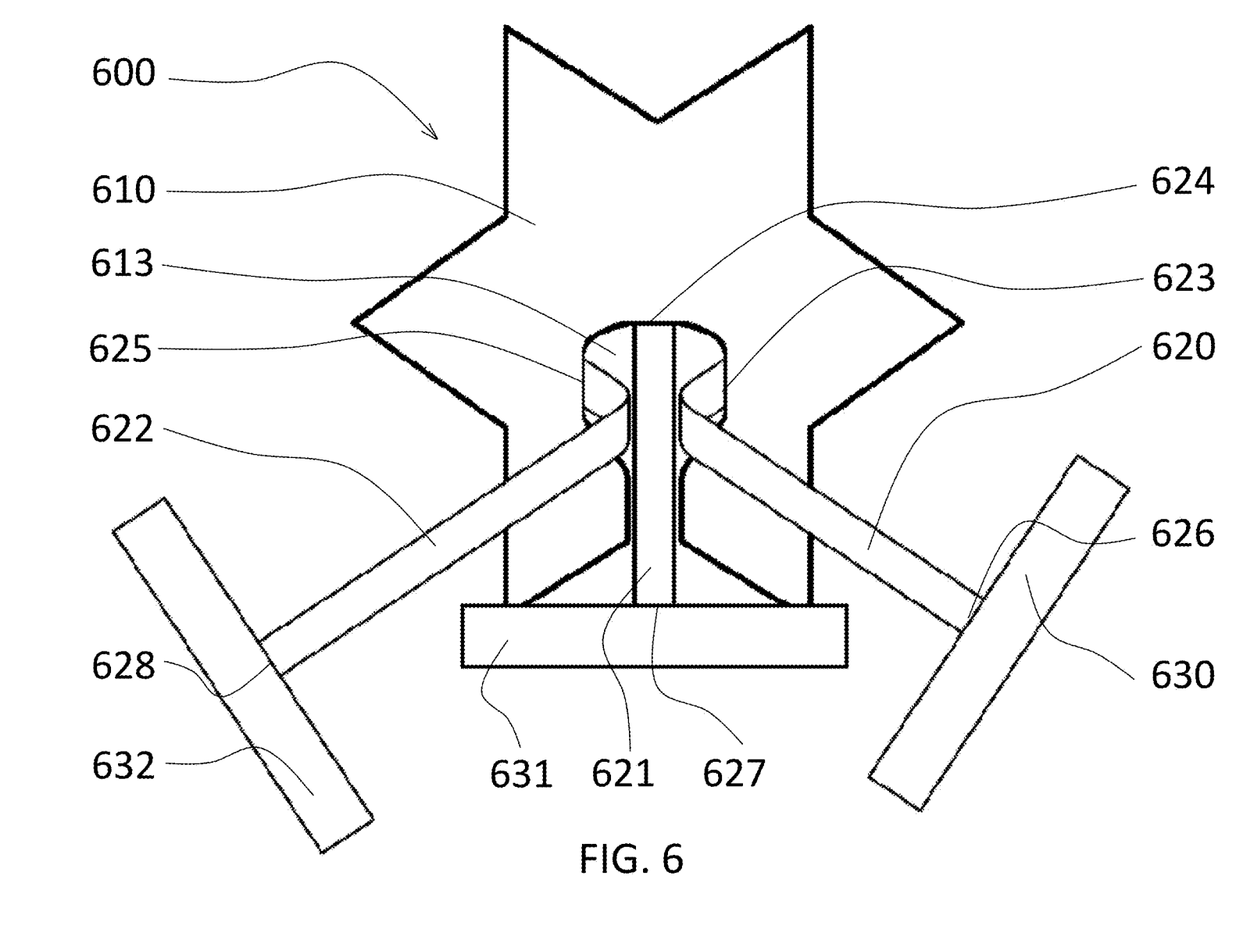
FIG. 6 illustrates a top view of a surgical dressing.

FIG. 6 illustrates a top view of a surgical dressing 600 having a dressing element 610, a plurality of connection elements, and a plurality of tube elements. The plurality of connection elements may include 1, 2, 3, 4, 5, 6, 7, 8, or more connection elements. The plurality of connection elements may include a first connection element 620, a second connection element 621, and a third connection element 622. The plurality of tube elements may include 1, 2, 3, 4, 5, 6, 7, 8, or more tube elements (e.g., one tube element for each connection element). The plurality of tube elements may include a first tube element 630, a second connection element 631, and a third connection element 632.

A slot 613 may be formed in dressing element 610. Slot 613 may extend from an outer perimeter of dressing element 610 to a discrete location within the interior of dressing element 610 (e.g., to an interior within a perimeter of dressing element 610). Dressing element 610 may have a particular shape (e.g., star-shaped), though any shape is possible that facilitates attachment of dressing element 610 to different kinds of wounds or to different contours of an organic body. Slot 613 may be wide enough to accommodate a plurality of tubes exiting a wound of an organic body (e.g., a tube for each connection element). Slot 613 may have a constant width or may have an irregular width. Slot 613 may have a narrower end (e.g., positioned near the perimeter of dressing element 610) and a wider end (e.g., positioned within the interior of dressing element 610), as exemplified in FIG. 6.

The plurality of connection elements may extend from within slot 613 to a plurality of tube elements, respectively. The plurality of connection elements may be secured at a common position within slot 613, may be secured around a perimeter of slot 613 (e.g., at a plurality of connection points within the wider end of slot 613), or at various other positions along dressing element 610 as presented in this disclosure. The plurality of connection elements may be regularly or irregularly spaced within slot 613. The plurality of connection elements may be positioned on similar or different sides of slot 613. The first connection element 620 may be secured to dressing element 610 at a first connection point 623 as described in this disclosure. The second connection element 621 may be secured to the dressing element 610 at a second connection point 624 as described in this disclosure. The third connection element 622 may be secured to the dressing element 610 at a third connection point 625 as described in this disclosure.

The plurality of connection elements may extend to respective ones of the plurality of tube elements. The plurality of connection elements may be of similar or different lengths, and may retain respective ones of the plurality of tube elements (e.g., 1, 2, 3, 4, 5, 6, 7, 8, or more tubes) at predetermined distances or positions with respect to dressing element 610. The first connection element 620 may be secured to the first tube element 630 at a fourth connection point 626 as described in this disclosure. The second connection element 621 may be secured to the second tube element 631 at a fifth connection point 627 as described in this disclosure. The third connection element 622 may be secured to the third tube element 632 at a sixth connection point 628 as described in this disclosure.

The plurality of tube elements may be dimensioned similarly or differently to accommodate attachment to tubes of various sizes and shapes. The plurality of tubes may exit from the same or different wounds. Slot 613 may be adequately shaped and dimensioned to enable the plurality of tubes to pass through dressing element 610 in an organized and/or tightly packed configuration.

Figure 7:
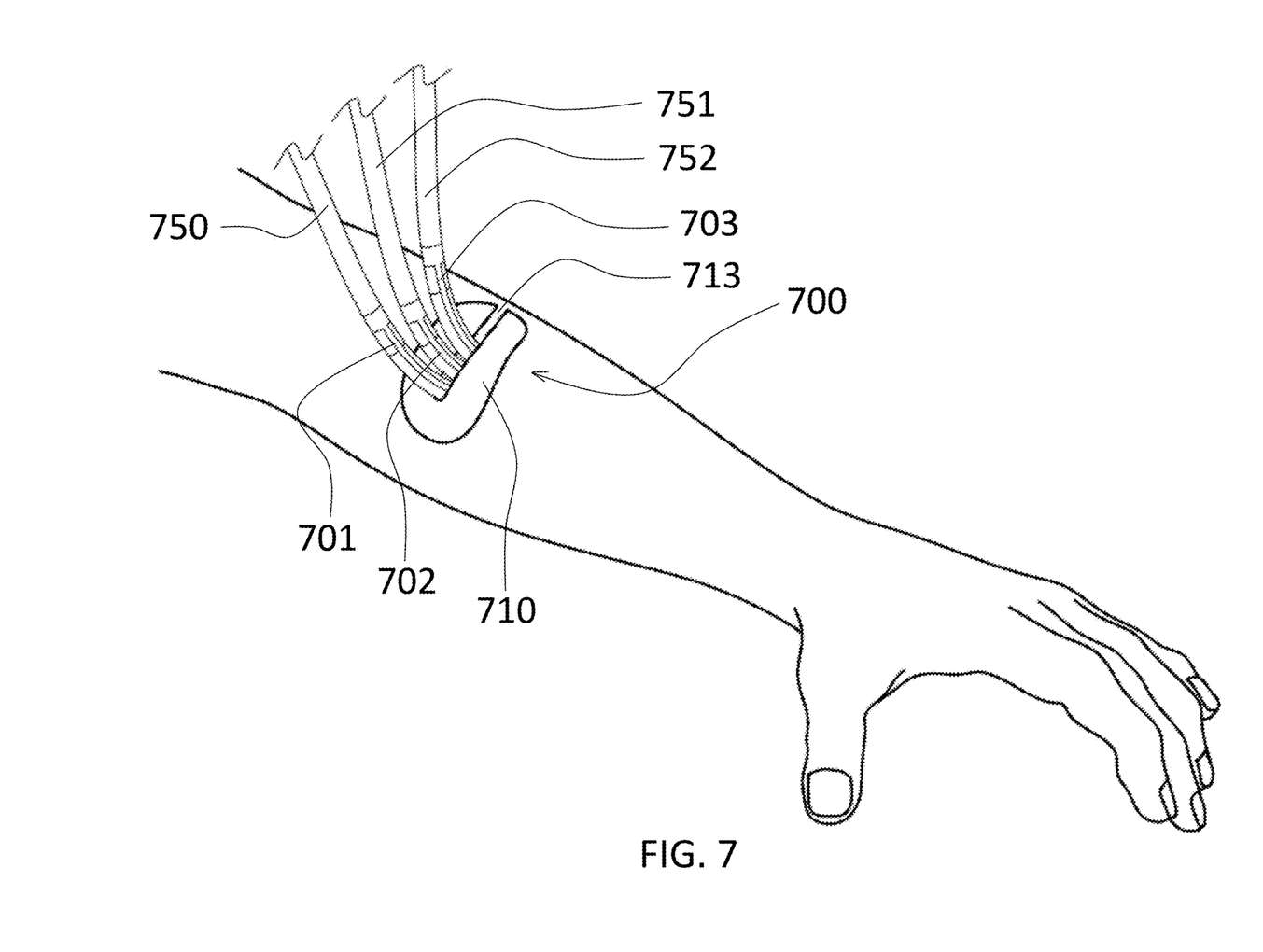
FIG. 7 illustrates an isometric view of a surgical dressing applied to a wound around a plurality of tubes.

FIG. 7 illustrates an isometric view of a surgical dressing 700 applied to a wound around a plurality of tubes (e.g., tubes 750, 751, 752). The surgical dressing 700 may include a dressing element 710 and a plurality of tube connection apparatuses (e.g., tube connection apparatuses 701, 702, 703). Surgical dressing 700 may include a tube connection apparatus for each of the plurality of tubes (e.g., 1, 2, 3, 4, 5, 6, 7, 8, or more tube connection apparatuses). Each tube connection apparatus may include a connection element and a tube element for attachment to one of the plurality of tubes as presented in this disclosure.

A slot 713 may be formed in dressing element 710 to accommodate the passage of the plurality of tubes. Slot 713 may extend from an outer perimeter of dressing element 710, and may extend a discrete distance within the interior of dressing element 710 (e.g., a specified distance for each tube of the plurality of tubes). Dressing element 710 may have a particular shape (e.g., oval or ovular), though any shape is possible that facilitates attachment of dressing element 710 to different contours of an organic body. Slot 713 may be only wide enough to accommodate the plurality of tubes in a single-file configuration (e.g., in a single row).

The plurality of tube connection apparatuses may extend from a perimeter of slot 713 to the plurality of tubes, respectively. The plurality of tube connection apparatuses may be secured along one side of the perimeter of slot 713. The first tube connection apparatus 701 may be secured to a first tube 750 to retain the tube 750 against movement with respect to the wound and/or the dressing element 710. The second tube connection apparatus 702 may be secured to a second tube 751 to retain the tube 751 against movement with respect to the wound and/or the dressing element 710. The third tube connection apparatus 703 may be secured to a third tube 752 to retain the tube 752 against movement with respect to the wound and/or the dressing element 710.

The plurality of tube connection apparatuses (e.g., 1, 2, 3, 4, 5, 6, 7, 8, or more tube connection apparatuses) may extend to respective ones of the plurality of tubes. The plurality of tube connection apparatuses may be of similar or different lengths (e.g., between about one inch and ten inches), and may retain respective ones of the plurality of tube elements at predetermined distances or positions with respect to dressing element 710. The plurality of tube connection apparatuses may be dimensioned similarly or differently to accommodate attachment to tubes of various sizes and shapes.

Figure 8:
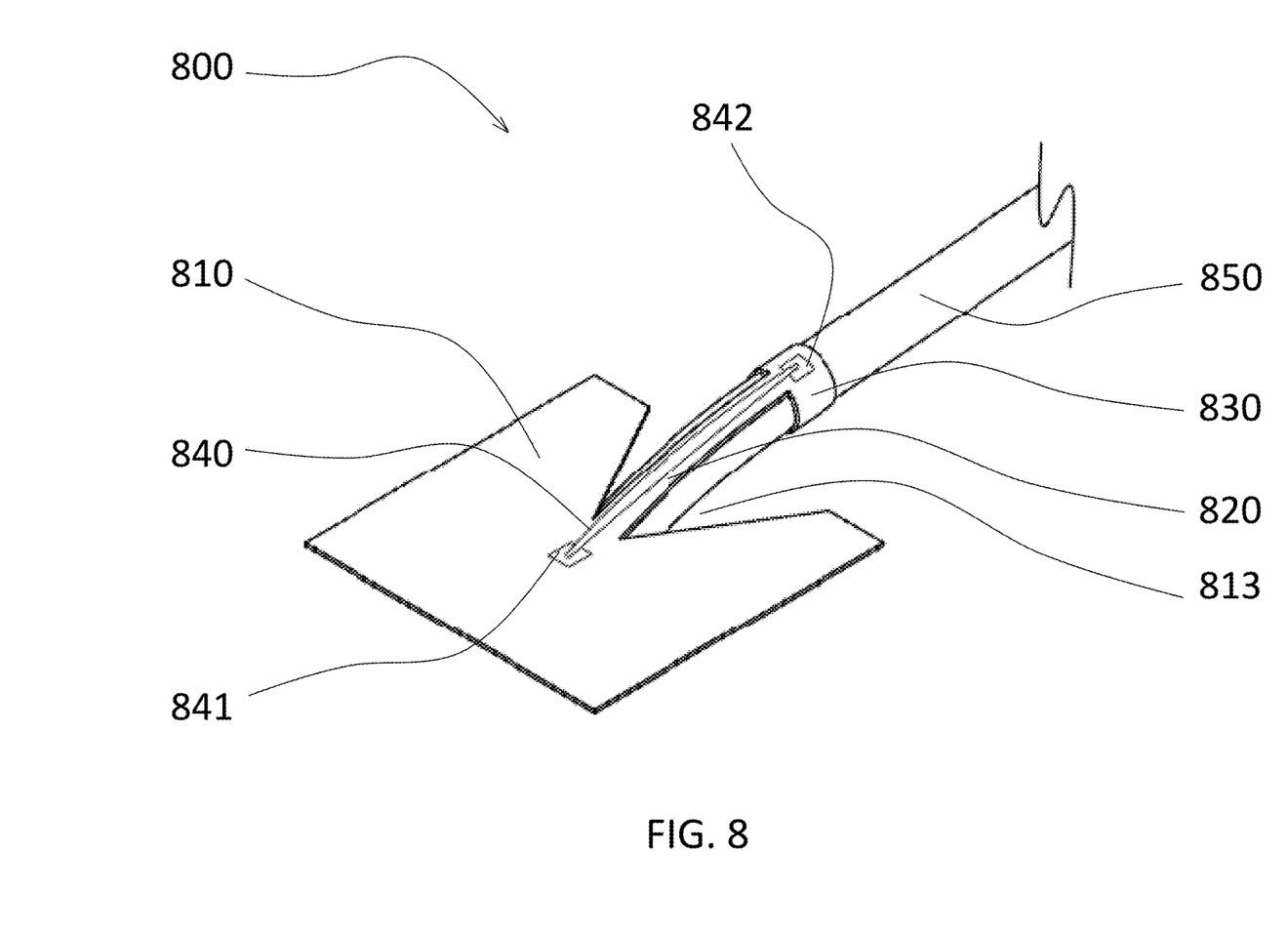
FIG. 8 illustrates an isometric view of a surgical dressing.

FIG. 8 illustrates an isometric view of a surgical dressing 800 having a dressing element 810, a connection element 820, and a tube element 830. Dressing element 810 may have a particular shape (e.g., square as exemplified in FIG. 8), though any shape is possible that facilitates attachment of dressing element 810 to different kinds of wounds. A slot 813 may be formed in dressing element 810 to allow passage of a tube 850 in close proximity to the connection element 820.

Dressing element 810 and tube element 830 may be coupled on opposing ends of connection element 820 (e.g., at one or more connection points). Connection element 820 may have relatively high elasticity to allow some stretching and/or retracting in response to movement of tube 850.

A secondary connection element 840 may extend from dressing element 810 to tube element 830. Secondary connection element 840 may extend approximately parallel to connection element 820. Secondary connection element 840 may be secured to dressing element 810 at a first connection point 841. Secondary connection element 840 may be secured to tube element 830 at a second connection point 842.

Secondary connection element 840 may be non-elastic and/or may have a relatively low elasticity. Secondary connection element 840 may be rigid. Secondary connection element 840 may enable connection element 820 to be pre-loaded with tensile forces (e.g., prior to application of surgical dressing 800 to the organic body). Secondary connection element 840 may be applied to dressing element 810 and/or tube element 830 while connection element 820 is in a stretched condition. Secondary connection element 840 may hold connection element 820 in the stretched condition until secondary connection element 840 is removed from dressing element 810 and/or tube element 830 (e.g., during application of surgical dressing 800 to the organic body). The stretched condition may correspond to a maximum stretch of connection element 820 without causing permanent damage to connection element 820. The stretched condition may correspond to an intermediate stretch of connection element 820 (e.g., between no stretch and the maximum stretch without causing damage to connection element 820). The stretched condition may correspond to a desired length of connection element 820 (e.g., such as a length corresponding to between a 10% and a 100% stretch, or more). The stretched condition may correspond to a desired amount of tensile and/or pre-loaded force (e.g., such as a force of between 10 lbs. and 0.1 lbs. or less).

During application of surgical dressing 800, dressing element 810 may be applied around a wound of an organic body in close proximity to a tube 850 extending from the wound. The connection element 820 and/or secondary connection element 840 may be aligned to extend along the tube 850. The tube element 830 may be attached, connected to, or affixed to the tube 850 to secure the tube 850 with respect to the surgical dressing 800. Finally, the secondary connection element 840 may be removed from surgical dressing 800 to allow stretching and/or relaxing of connection element 820 in response to forces exerted on tube 850.

The secondary connection element 840 may be removed in any suitable manner, including, without limitation, being clipped or snipped, snapping (e.g., at a breakaway portion), decoupling at the first connection point 841 and/or second connection point 842, and so forth. While secondary connection element 840 may be contemplated as a coating, or layer affixed along the length of connection element 820 (e.g., adhered to connection element 820), secondary connection element 840 may be contemplated as a wholly independent structural element that need not come into contact with connection element 820, or that may contact connection element 820 only incidentally (e.g., coupled to dressing element 810 and tube element 830).

Figure 9:
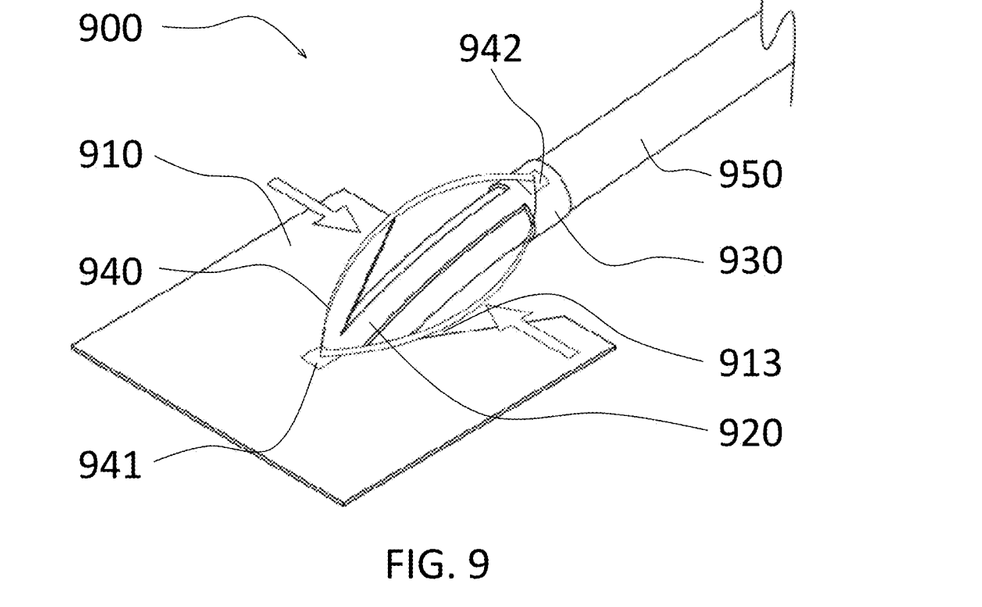
FIG. 9 illustrates an isometric view of a surgical dressing.
Figure 10:
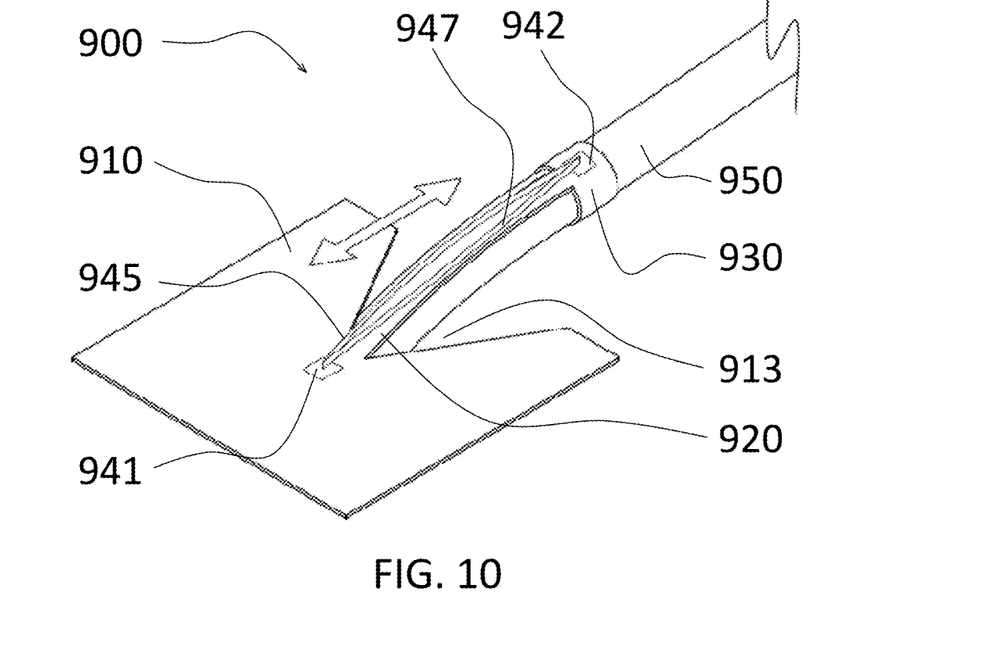
FIG. 10 illustrates an isometric view of a surgical dressing.

FIGS. 9 and 10 illustrate isometric views of a surgical dressing 900 having a dressing element 910, a connection element 920, and a tube element 930. Dressing element 910 may have any suitable shape to facilitate attachment of dressing element 910 to different kinds of wounds or surfaces. A concavity 913 may be formed in a perimeter of dressing element 910 to allow passage of a tube 950 in close proximity to the connection element 920.

Dressing element 910 and tube element 930 may be coupled on opposing ends of connection element 920 (e.g., at one or more connection points). Connection element 920 may have relatively high elasticity to allow some stretching and/or retracting in response to movement of tube 950.

A secondary connection element 940 may extend from dressing element 910 to tube element 930. Secondary connection element 940 may be secured to dressing element 910 at a first connection point 941. Secondary connection element 940 may be secured to tube element 930 at a second connection point 942. Secondary connection element 940 may include one or more elements (e.g., a first element 945 and/or a second element 947) with relatively high elasticity to allow some bending in response to movement of tube 950. The one or more elements may be constructed to extend linearly from dressing element 910 to tube element 930. The one or more elements may be constructed to extend nonlinearly (e.g., having an arcuate or bowed path) from dressing element 910 to tube element 930. A first element 945 may extend arcuately from dressing element 910 to tube element 930. A second element 947 may extend arcuately from dressing element 910 to tube element 930. The path of first element 945 and the path of second element 947 may be symmetrical (e.g., on either side of a line extending from first connection point 941 on dressing element 910 to second connection point 942 on tube element 930, so as to form a double-bowed shape).

Though the elements 945, 947 are illustrated following an arcuate path, other nonlinear and non-arcuate paths are contemplated by this disclosure. Though the elements 945, 947 are illustrated as symmetrical, other non-symmetrical paths are contemplated by this disclosure. Though the secondary connection element 940 is illustrated with two flexible elements, less or more elements are contemplated by this disclosure (e.g., 1, 2, 3, 4, 5, or more elements). A person of ordinary skill in the art will appreciate that it may be desirable to retain tube 950 in a particular way (e.g., extending in a particular direction, or at a particular position with respect to the organic body), and that the precise construction of the one or more elements may be modified to achieve the desired retention of tube 950.

Secondary connection element 940 may enable connection element 920 to be pre-loaded with tensile forces as heretofore disclosed, though this need not be the case. Secondary connection element 940 may be applied to dressing element 910 and/or tube element 930 while connection element 920 is in a fully stretched position, in an intermediate position, or in a zero-stretch position.

During application of surgical dressing 900, dressing element 910 may be applied around a wound of an organic body in close proximity to the tube 950 extending from the wound. The connection element 920 and/or secondary connection element 940 may be aligned to extend along the tube 950. The tube element 930 may be attached, connected to, or affixed to the tube 950 to secure the tube 950 with respect to the surgical dressing 900. Once in place, the connection element 920 and secondary connection element 940 may be stretched and/or relaxed in response to forces exerted on tube 950.

A force applied to tube 950 may cause tube 950 to be pushed toward the wound. In this scenario, second connection point 942 may move closer to first connection point 941, or vice versa. In this scenario, the tension in connection element 920 may be relaxed. In this scenario, the length of connection element 920 may be shortened. In this scenario, the tensile force exerted by connection element 920 may be reduced. Further, in this scenario, the secondary connection element 940 (e.g., the first and second elements 945, 947) may experience greater bending. In this scenario, the secondary connection element 940 may experience an increase in tensile force. In this scenario, the one or more elements of secondary connection element 940 may undergo a reduction in the radius of the arcuate path of each of the one or more elements. In this scenario, the one or more elements of secondary connection element 940 may experience greater deflection.

A force applied to tube 950 may cause tube 950 to be pulled away from the wound. In this scenario, second connection point 942 may move away from first connection point 941, or vice versa. In this scenario, the tension in connection element 920 may be increased. In this scenario, the length of connection element 920 may be lengthened. In this scenario, the tensile force exerted by connection element 920 may be increased. Further, in this scenario, the secondary connection element 940 (e.g., the first and second elements 945, 947) may experience less bending. In this scenario, the secondary connection element 940 may experience a decrease in tensile force. In this scenario, the one or more elements of secondary connection element 940 may undergo an increase in the radius of the arcuate path of each of the one or more elements. In this scenario, the one or more elements of secondary connection element 940 may experience less deflection.

Other aspects will be apparent to those skilled in the art from consideration of the specification and practice disclosed herein. It is intended, therefore, that the specification and illustrated figures be considered as examples only.

What is claimed is:

1. A surgical dressing configured to be applied over a wound of an organic body, the surgical dressing located in proximity to one or more tubes, the surgical dressing comprising:
   a dressing element configured to be adhered to the organic body, the dressing element having a slot extending into an interior;
   a first connection element extending from the dressing element, the first connection element extendable along the one or more tubes, wherein the first connection element is elastic, wherein the first connection element is coupled at a position within the slot; and
   a first tube element extending from the first connection element, the first tube element couplable to the one or more tubes, wherein the first connection element is capable of stretching to absorb a force exerted on the one or more tubes.

2. The surgical dressing of claim 1, further including a secondary layer adhered along a length of the first connection element, wherein the first connection element is capable of stretching to absorb the force exerted on the one or more tubes after the secondary layer is removed.

3. The surgical dressing of claim 1, further including a secondary connection element extending along a length of the first connection element, wherein the secondary connection element retains the first connection element in a stretched condition, wherein the first connection element is capable of stretching to absorb the force exerted on the one or more tubes after the secondary connection element is removed.

4. The surgical dressing of claim 3, wherein the stretched condition of the first connection element corresponds to one of a desired length of the first connection element and a desired amount of pre-loaded tensile force exerted by the first connection element.

5. The surgical dressing of claim 1, further including a secondary connection element extending along a length of the first connection element, wherein the secondary connection element and the first connection element retain the one or more tubes in a desired position, wherein the first connection element is capable of stretching and/or relaxing to absorb the force exerted on the one or more tubes, and wherein the secondary connection element is capable of bending to absorb the force exerted on the one or more tubes.

6. The surgical dressing of claim 1, further including:
   a second connection element extending from the dressing element, the second connection element extendable along the one or more tubes, wherein the second connection element is elastic; and
   a second tube element extending from the second connection element, the first and second tube elements couplable to respective ones of the one or more tubes, wherein the second connection element is capable of stretching to absorb the force exerted on the one or more tubes.

7. The surgical dressing of claim 1, further including:
   a second connection element extending from the dressing element, the second connection element extendable along the one or more tubes, wherein the second connection element is elastic, wherein the second connection element extends to the first tube element, wherein the second connection element is capable of stretching to absorb the force exerted on the one or more tubes.

8. The surgical dressing of claim 1, wherein the dressing element is formed of a plurality of layers, wherein the plurality of layers includes one or more of an outer layer, a middle layer, a contact layer, a structural layer, an antibacterial layer, an absorbent layer, a padded layer, a compression bandage layer, a semipermeable layer, a shape-conforming layer, a gauze layer, a lint layer, a cotton layer, a wool layer, a plaster layer, and a synthetic polymer layer.

9. The surgical dressing of claim 1, wherein the first connection element is capable of stretching to between 10% and 100% of its length in response to an applied force.

10. A surgical dressing configured to be applied over a wound of an organic body, the surgical dressing located in proximity to a tube, the surgical dressing comprising:
   a dressing element configured to be adhered to the organic body, the dressing element having a slot extending into an interior;
   a connection element extending from the dressing element, the connection element extendable along the tube, wherein the connection element is elastic, wherein the connection element is coupled at a position within the slot;

a tube element extending from the connection element, the tube element couplable to the tube; and a secondary element extending from the dressing element to the tube element along a length of the connection element, wherein the connection element is capable of stretching to absorb a force exerted on the tube after the secondary element is removed.

11. The surgical dressing of claim 10, wherein the secondary element retains the connection element in a stretched condition.

12. The surgical dressing of claim 11, wherein the stretched condition of the connection element corresponds to one of a desired length of the connection element and a desired amount of pre-loaded tensile force exerted by the connection element.

13. The surgical dressing of claim 10, wherein the secondary element is removable, wherein the connection element is retained in a stretched condition by the secondary element, and wherein when the secondary element is removed the connection element exerts the force on the tube.

14. The surgical dressing of claim 10, wherein the secondary element includes one or more flexible elements, wherein the one or more flexible elements bend in response to forces exerted on the tube.

15. The surgical dressing of claim 14, wherein the one or more flexible elements includes a first element and a second element, the first and second elements extending from the dressing element to the tube element along nonlinear paths.

16. A method of manufacturing a tube connection surgical dressing for application over a wound of an organic body in proximity to a tube, the method comprising:

selecting a planar element having an exterior and an interior;

forming a slot in the planar element extending from the exterior to the interior to create a dressing element;

forming a connection element capable of extending along the tube, wherein the connection element is elastic, wherein the connection element is coupled to the dressing element at a position within the slot at a first connection end; and forming a tube element extending from the connection element at a second connection end, the tube element capable of being coupled to the tube, wherein the connection element is capable of stretching to absorb a force exerted on the tube.

17. The method of claim 16, further including:

forming a dressing element capable of being applied to the organic body; and attaching the connection element to the dressing element so that the connection element extends from the dressing element.

18. The method of claim 16, further including forming a secondary element extending from the dressing element to the tube element along a length of the connection element, wherein the connection element is capable of stretching to absorb the force exerted on the tube after the secondary element is removed.

19. The method of claim 16, further including:

forming a secondary connection element extending a length of the connection element, wherein the connection element and the secondary connection element retain the tube in a desired position, wherein the connection element is capable of stretching and/or relaxing to absorb the force exerted on the tube, and wherein the secondary connection element is capable of bending to absorb the force exerted on the tube.

* * * * *